(12) United States Patent
Charles

(10) Patent No.: US 7,141,048 B1
(45) Date of Patent: Nov. 28, 2006

(54) VITREORETINAL INSTRUMENT

(75) Inventor: Steven T. Charles, Memphis, TN (US)

(73) Assignee: Alcon, Inc., Hunenberg (CH)

( * ) Notice: Subject to any disclaimer, the term of this patent is extended or adjusted under 35 U.S.C. 154(b) by 408 days.

(21) Appl. No.: 10/672,612

(22) Filed: Sep. 26, 2003

Related U.S. Application Data

(60) Provisional application No. 60/419,272, filed on Oct. 17, 2002.

(51) Int. Cl.
*A61B 18/18* (2006.01)
*A61M 5/00* (2006.01)

(52) U.S. Cl. .......................... 606/4; 606/166; 604/264

(58) Field of Classification Search .................. 606/4, 606/6, 166; 604/14, 20, 21, 27, 28, 264, 604/268, 273, 274; 362/551, 553–556, 562, 362/572
See application file for complete search history.

(56) References Cited

U.S. PATENT DOCUMENTS

| | | | | |
|---|---|---|---|---|
| 5,545,153 A | * | 8/1996 | Grinblat et al. | 604/294 |
| 5,688,264 A | * | 11/1997 | Ren et al. | 606/15 |
| 5,817,075 A | * | 10/1998 | Giungo | 604/294 |
| 6,413,245 B1 | * | 7/2002 | Yaacobi et al. | 604/264 |
| 6,514,238 B1 | * | 2/2003 | Hughes | 606/1 |
| 6,524,275 B1 | * | 2/2003 | Lynch et al. | 604/96.01 |
| 6,579,256 B1 | * | 6/2003 | Hughes | 604/60 |
| 2004/0039253 A1 | | 2/2004 | Peyman et al. | |
| 2005/0261624 A1 | * | 11/2005 | Wilcox | 604/27 |

OTHER PUBLICATIONS

Alcon 2001 Vitreoretinal Product Catalog, p. 23, item 11 "Small Gauge Retinal Needle".

* cited by examiner

*Primary Examiner*—A. Farah
(74) *Attorney, Agent, or Firm*—W. David Lee

(57) ABSTRACT

An improved instrument for helping to remove subretinal fluid and helping to perform fluid exchanges in vitreoretinal surgery is disclosed. The instrument includes a handle and a probe coupled to the handle. The probe includes a curved distal portion having a closed tip with a smooth surface capable of safely touching the retina.

2 Claims, 1 Drawing Sheet

VITREORETINAL INSTRUMENT

This application claims the priority of U.S. Provisional Application No. 60/419,272 filed Oct. 17, 2002.

FIELD OF THE INVENTION

The present invention generally pertains to vitreoretinal surgery and more particularly to improved instruments suitable for helping to remove subretinal fluid and helping to perform fluid exchanges typically used in such surgeries.

DESCRIPTION OF THE RELATED ART

In a healthy human eye, the retina is physically attached to the choroid in a generally circumferential manner behind the pars plana. The vitreous humor, a transparent jelly-like material that fills the posterior segment of the eye, helps to cause the remainder of the retina to lie against, but not physically attach, to the choroid.

Sometimes a portion of the retina becomes detached from the choroid. Other times a portion of the retina may tear, allowing vitreous humor, and sometimes aqueous humor, to flow between the retina and the choroid, creating a build up of subretinal fluid. Both of these conditions result in a loss of vision.

To surgically repair these conditions, a surgeon typically inserts a vitrectomy probe into the posterior segment of the eye via a scleratomy, an incision through the sclera at the pars plana. The surgeon typically also inserts a fiber optic light source and an infusion cannula into the eye via similar incisions, and may sometimes substitute an aspiration probe for the vitrectomy probe. While viewing the posterior segment under a microscope and with the aid of the fiber optic light source, the surgeon cuts and aspirates away vitreous using the vitrectomy probe to gain access to the retinal detachment or tear. The surgeon may also use the vitrectomy probe, scissors, a pick, and/or forceps to remove any membrane that has contributed to the retinal detachment or tear. During this portion of the surgery, a saline solution is typically infused into the eye via the infusion cannula to maintain the appropriate intraocular pressure.

Next, the surgeon must manipulate the detached or torn portion of the retina to flatten against the choroid in the proper location. A soft tip cannula, forceps, or pick is typically utilized for such manipulation. Many surgeons also inject perfluorocarbon liquid as a retinal tamponading fluid into the posterior segment of the eye while aspirating the saline solution in the posterior segment to help cause the detached or torn portion of the retina to flatten against the choroid in the proper location. This procedure is typically referred to as a "fluid/perfluorocarbon" exchange. Other surgeons inject air as a retinal tamponading fluid into the posterior segment of the eye while aspirating the saline solution. This procedure is typically referred to as a "fluid/ air" exchange. Finally, other surgeons inject a mixture of air and a gas such as $SF_6$, $C_3F_8$, or $C_2F_6$ as a retinal tamponading fluid into the posterior segment of the eye while aspirating the saline solution. This procedure is typically referred to as a "fluid/gas" exchange. As used herein, a "fluid" may include any liquid or gas that is suitable for use in the eye, including, but not limited to, saline solution with or without additives, silicone oil, a perfluorocarbon liquid, air, or a perfluorocarbon gas.

After performing one of the above-described "fluid/fluid" exchanges, the surgeon then typically drains any sub-retinal fluid present between the retina and the choroid. Conventionally, the vacuum port of a vitrectomy probe; a blunt tipped, straight cannula having a port on its distal tip; blunt-tipped cannulas or sharp-tipped needles having a straight proximal portion, an angulated or slanted distal portion, and a port on their distal tips; and a soft tip, cannulated flute needle have all been used to drain subretinal fluid. The literature also mentions a curved cannula having a radius of curvature of the human eye and a single port on its ventral surface near its tip for the drainage of subretinal fluid. The literature further mentions a curved cannula having a radius of curvature of the human eye, a port on its ventral surface near its tip for the drainage of subretinal fluid, and a second port on its dorsal surface spaced away from its tip for supporting a "fluid/gas" exchange. Such instruments may be connected to a conventional syringe, a flute needle handle, or to an aspiration port of a surgical cassette that is operatively coupled to an ophthalmic surgical console. Such instruments gain access to the subretinal space via an existing retinal tear, a surgical excision of a piece of retina (retinectomy), or a surgical incision through the retina (retinotomy). After the detached or torn portion of the retina is properly located and the subretinal fluid is drained, the surgeon typically uses a diathermy probe or a laser to create a scar that, when healed, holds portions of the detached retina in place.

However, a need still exists in vitreoretinal surgery for an improved instrument for helping to displace or express subretinal fluid, mobilize and/or smooth out retinal folds, unfold retinal tears and/or retinectomy flaps, or help to cause the retina to flatten against the choroid in the proper location. The instrument should be easy for the surgeon to use, should maximize patient safety, and should be economically feasible.

SUMMARY OF THE INVENTION

One aspect of the present invention comprises a vitreoretinal instrument including a handle and a probe coupled to the handle. The probe includes a curved distal portion having a closed tip with a smooth surface capable of safely touching the retina.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

Figure 1:
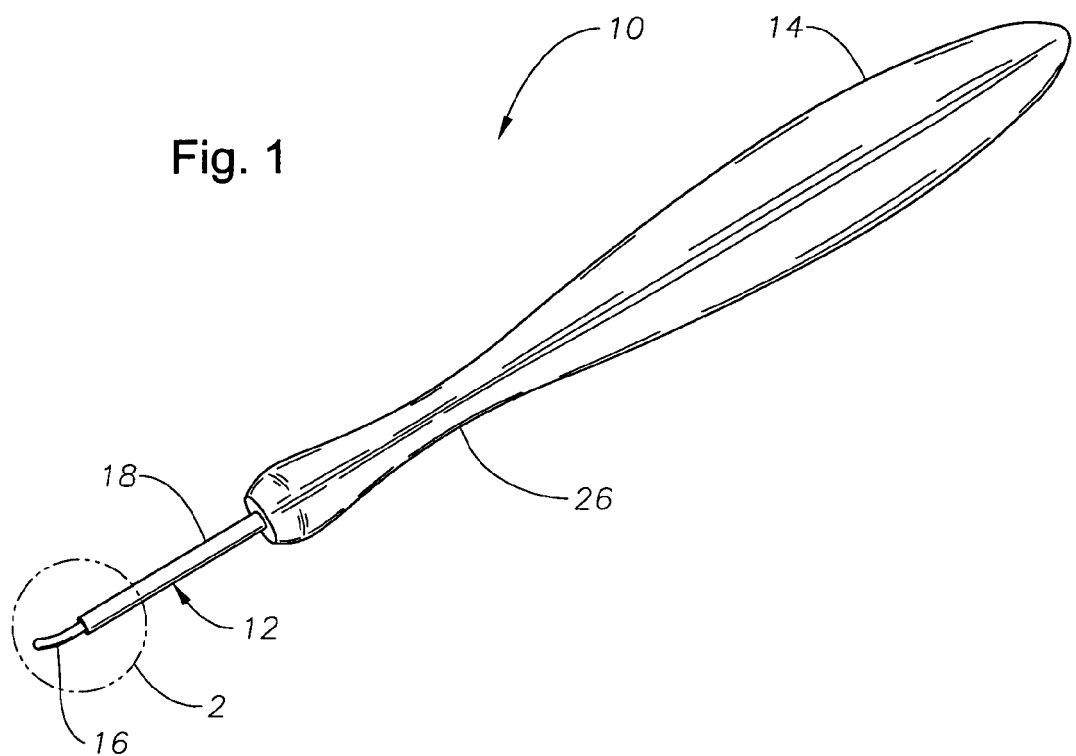
FIG. 1 is a perspective view of an instrument according to a preferred embodiment of the present invention.
Figure 2:
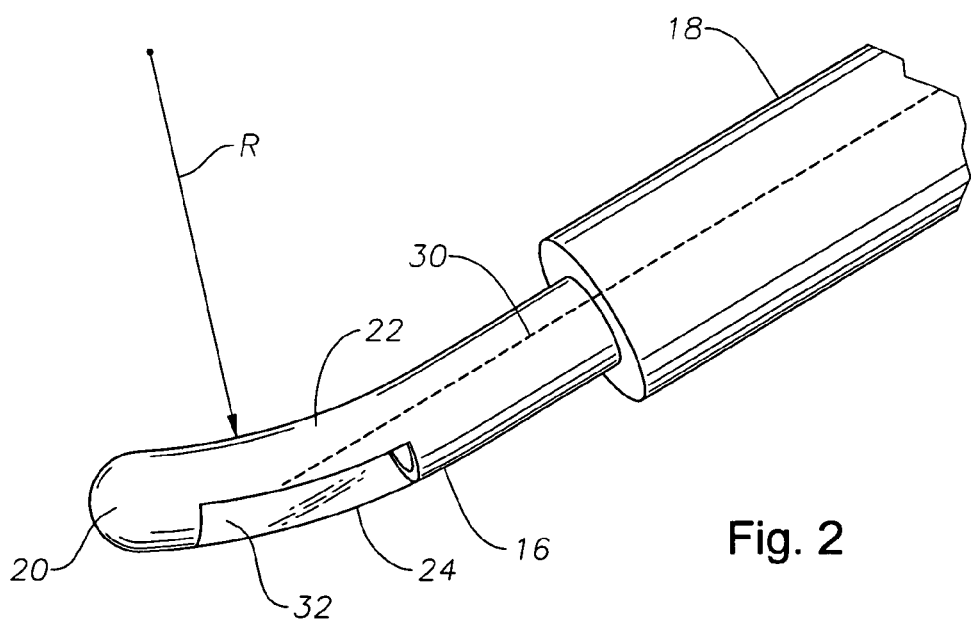
FIG. 2 is an enlarged, perspective, schematic view of the probe of the instrument of FIG. 1 taken at circle 2 in FIG. 1.

The preferred embodiments of the present invention and their advantages are best understood by referring to FIGS. 1 through 2 of the drawings, like numerals being used for like and corresponding parts of the various drawings.

Instrument 10 generally includes a probe 12 on its distal end and a handle 14 on its proximal end. Probe 12 may have a solid interior or may be formed as a cannula. Probe 12 preferably includes a curved, distal portion 16 and a straight, proximal portion 18. Curved portion 16 preferably has a radius of curvature R substantially equal to the radius of curvature of the human eye. Curved portion 16 also preferably has a closed tip 20 having a convex surface for interfacing with the retina. Curved portion 16 has a ventral surface 22 and a dorsal surface 24. Ventral surface 22 and dorsal surface 24 preferably each form a 180 degree arc from a longitudinal axis of curved portion 16. Curved portion 16 is preferably made of a flexible thermoplastic such as a polyamide. The surface of tip 20, as well as ventral surface 22 and dorsal surface 24, are very smooth and have very low friction to avoid damage to the retina. In addition, the surface of tip 20, as well as ventral surface 22 and dorsal surface 24, may optionally be coated with or made from Teflon, silicone, or other friction reducing material to avoid adherence to the retina, retinal pigment epithelium, or choroid. Probe 12 is sufficiently long to contact the retina in a highly myopic eye. Straight portion 18 is preferably about 20 to about 25 gauge and is preferably made of a metal such as stainless steel.

Handle 14 preferably includes an area 26 having a smaller cross-section to facilitate a surgeon grasping handle 14 between his or her thumb, index finger, and middle finger using a pencil-like grip. Handle 14 thus preferably has an "hourglass shape". Area 26 may also be roughened, textured, or knurled to facilitate a surgeon's grip. Handle 14 preferably has a length so that it rests in the web of skin between a surgeon's thumb and index finger when the surgeon grips handle 14 at area 26 as described above. Handle 14 is preferably light weight and is preferably integrally formed with probe 12.

An optical fiber 30 may optionally be disposed in handle 14 and straight portion 18 so as to terminate in curved portion 16. In this case, curved portion 16 may be formed with a light transmitting window 32, or may be formed from a light transmitting plastic, so that instrument 10 can provide intraocular illumination for the surgeon when fiber 30 is operatively coupled to a light source. Such light transmitting window 32 or light transmitting plastic are preferably substantially transparent.

After performing a vitrectomy to gain access to a retinal detachment or tear, a surgeon may use instrument 10 to help remove subretinal fluid or to help perform a fluid exchange in the following preferred manner. The surgeon may use tip 20, ventral surface 22, and/or dorsal surface 24 of curved portion 16 to displace or express subretinal fluid, mobilize and/or smooth out retinal folds, unfold retinal tears and/or retinectomy flaps, or help to cause the retina to flatten against the choroid in the proper location. When using dorsal surface 24 to displace subretinal fluid, the surgeon preferably disposes probe 12 within a vitreous cavity of the eye above a retinal detachment or tear with dorsal surface 24 closest to an inner surface of the retina. The surgeon then moves handle 14 using a "squeegee-like" motion so that dorsal surface 24 contacts the inner surface of the retina and displaces subretinal fluid. In addition, the surgeon may activate optical fiber 30 to provide intraocular illumination. Instrument 10 thus allows the surgeon to hold a microsurgical instrument other than an endoilluminator with his or her other hand, if desired.

From the above, it may be appreciated that the present invention provides improved apparatus and methods for helping to remove subretinal fluid and helping to perform fluid exchanges in vitreoretinal surgery. The instrument is easy for a surgeon to use and may be made in an economical manner. The instrument is preferably disposable, but may also be designed for limited re-use. The instrument maximizes patient safety as well as the success of the surgical procedure by facilitating complete removal of subretinal fluid; preventing or reducing the likelihood of retina, retinal pigment epithelium, or choroid damage; and facilitating the proper repositioning of retinal tears, detachments, or folds.

The present invention is illustrated herein by example, and various modifications may be made by a person of ordinary skill in the art. As an example, the present invention may also be used to gently break retinal—retinal adhesions and open up retinal folds caused by epiretinal membranes in diseases such as proliferative vitreoretinopathy. As another example, the present invention may be used in retinal or macular translocation surgery for the intentional creation of a retinal detachment and the displacement of the retina by creation and manipulation of retinal folds. As a further example, the present invention may be used to gently reposition dislocated intraocular lenses or to manipulate intraocular foreign bodies prior to removal. As a further example, the present invention is also applicable to other types of surgeries other than vitreoretinal surgery.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of displacing subretinal fluid from a space between a retinal detachment or a retinal tear and a choroid of an eye, comprising the steps of:

providing an vitreoretinal instrument, comprising:
  a handle; and
  a probe coupled to said handle comprising a curved distal portion made from a flexible plastic, said curved distal portion having a smooth dorsal surface capable of safely touching the retina;

grasping said handle;

disposing said probe within a vitreous cavity of said eye above said retinal detachment or retinal tear with said dorsal surface proximate an inner surface of said retina; and moving said handle so that said dorsal surface contacts said inner surface of said retina and displaces subretinal fluid.

2. The method of claim 1 wherein said probe comprises an optical fiber disposed in said handle and said curved portion, and further comprising the step of transmitting light from said optical fiber and said curved portion to an interior of said eye.

* * * * *